United States Patent [19]
Nelson et al.

[11] Patent Number: 4,819,489
[45] Date of Patent: Apr. 11, 1989

[54] DEVICE AND METHOD FOR TESTING THE ADHERENCE OF A COATING LAYER TO A MATERIAL

[75] Inventors: Jordan R. Nelson, Pennington; Gilbert L. Green, Sr., Trenton, both of N.J.; Randall E. McCoy, McConnellsburg, Pa.; Richard Williams, Princeton, N.J.

[73] Assignee: RCA Licensing Corp., Princeton, N.J.

[21] Appl. No.: 191,453

[22] Filed: May 9, 1988

[51] Int. Cl.⁴ .......................... G01N 3/20; B05L 11/00
[52] U.S. Cl. .................................... 73/854; 73/150 A; 118/73
[58] Field of Search ............. 73/849, 851, 854, 150 A; 427/8, 9; 118/713, 712, 73

[56] References Cited

U.S. PATENT DOCUMENTS

| | | | |
|---|---|---|---|
| 2,528,918 | 11/1950 | Stanius | 73/854 |
| 3,968,280 | 7/1976 | Poppe et al. | 427/195 |
| 4,539,286 | 9/1985 | Lipson et al. | 430/281 |

Primary Examiner—Michael J. Tokar
Assistant Examiner—Robert R. Raevis
Attorney, Agent, or Firm—E. M. Whitacre; D. H. Irlbeck; L. L. Hallacher

[57] ABSTRACT

A device for testing the adherence of a coating to a material includes a cone section and roller for bending the material around the cone section. The bent piece has a sharp bend at one end and a gradual bend at the other end. The proximity to the sharp bend at which flaking of the coating from the substrate occurs is a measure of the adherence of the coating to the material.

11 Claims, 3 Drawing Sheets

DEVICE AND METHOD FOR TESTING THE ADHERENCE OF A COATING LAYER TO A MATERIAL

BACKGROUND

This invention relates to the testing of the adherence of a coating to a sheet of material.

Various types of coatings are used extensively in the electronics and metal fabrication industries to protect or prime a metal surface. The coatings can be applied by controlled oxidation methods, glow discharge, electrodeposition, sputtering and painting. Irrespective of the nature of the coating and the metal surface, an important concern is the adherence of the coating to the metal substrate. Poor adherence almost invariably results in poor product. An example of an area where the proper adherence of an oxide coating to a metal substrate is important is the blackening oxide coating which is applied to the aluminum-killed steel used for shadow masks in cathode ray tubes.

Testing procedures presently available for testing adherence are not fully satisfactory. Typically, in the existing test procedure an element is affixed to the coated material using an epoxy or some other adhesive. The element is then pulled free from the substrate and microscopically examined to determine whether the element broke free from the coating, or whether the coating broke from the substrate. This type of testing is very sensitive to the angle of pull and the pull rate, the coverage area of the epoxy, and in the case of a poorly adhering coating, the epoxy can penetrate the coating and adhere directly to the metal substrate. For these reasons the test is not completely reliable for accurately determining the adherence of an oxide coating to a metallic substrate. There therefore is a need for a device for testing the adherence of a coating layer to a material substrate. The present invention fulfills this need.

SUMMARY

A device for testing the adherence of a coating layer to a material includes a base member having a support surface and a guide member supported by the support surface. The guide member has a tapered thickness to form a tapered surface. A cone section has a preselected angle and rests on the tapered surface at a preselected distance from the tapered surface to form a guide slot for guiding the material between the cone section and the tapered surface. Actuation means is pivotally attached to the base member. A bending means is actuated by the actuation means and bends the material around the cone section to form a tapered bend in the material.

DETAILED DESCRIPTION

Figure 1:
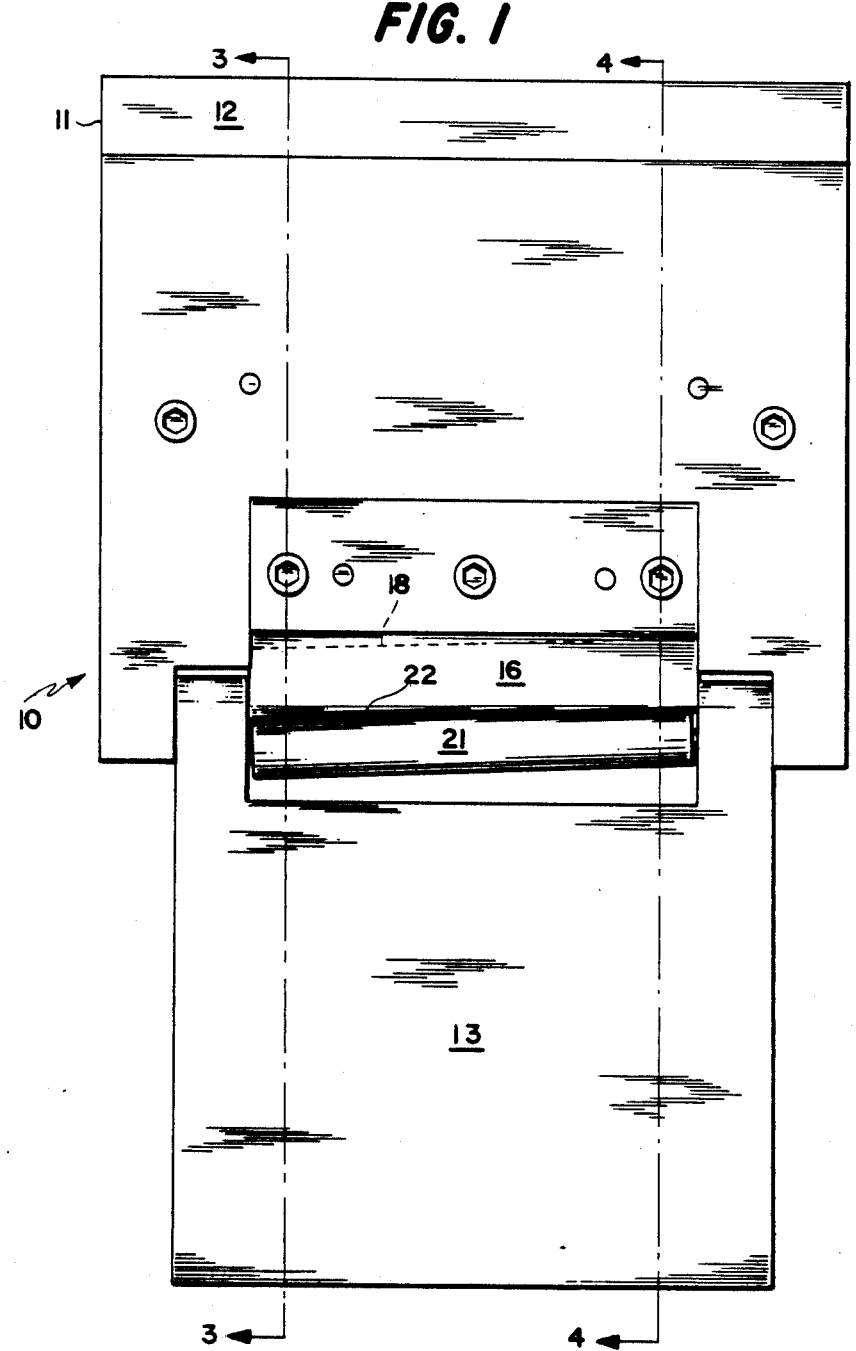
FIG. 1 is a top view of a preferred embodiment.

FIG. 1 shows a device 10 for testing the adherence of a coating layer to a material. The device 10 includes a base member 11 having a support surface 12. An actuating means 13 is pivotally coupled to the base member 11.

Figure 4:
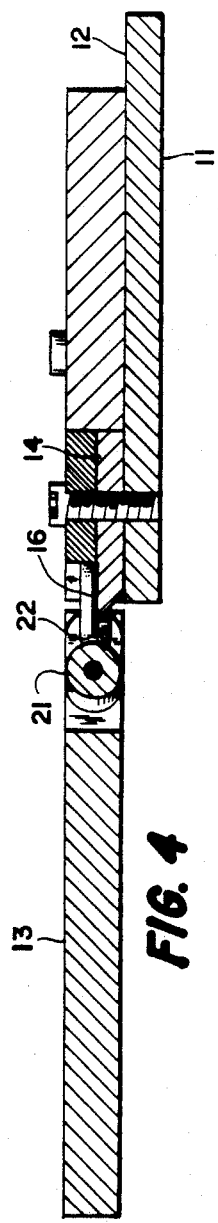
FIG. 4 is a cross section taken along line 4—4 of FIG. 1.
Figure 3:
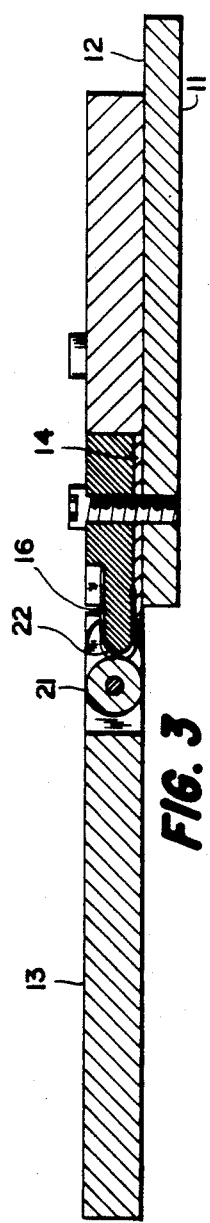
FIG. 3 is a cross section taken along line 3—3 of FIG. 1.
Figure 5:
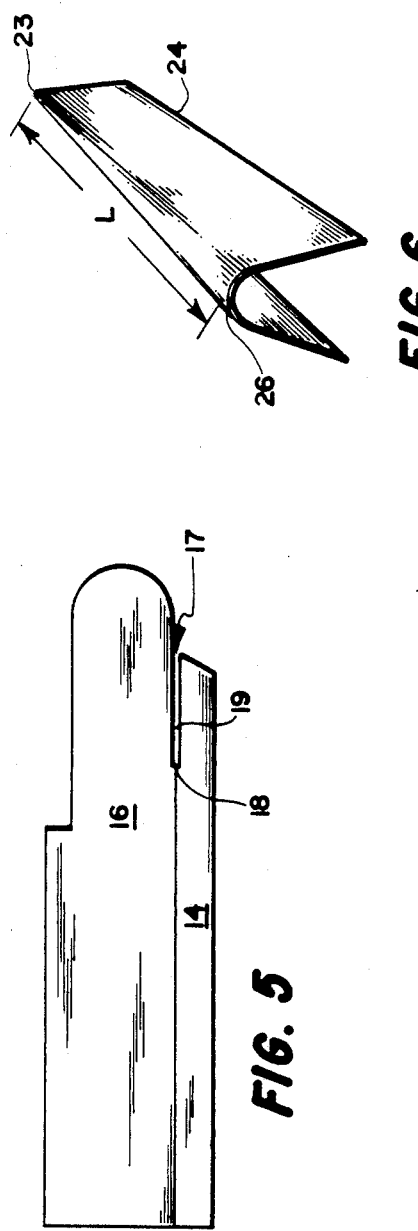
FIG. 5 is an enlarged view showing the tapered surface and cone section together.

In FIGS. 3 and 4, a guide member 14 is supported by the support surface 12. The guide member 14 is tapered, as indicated by the difference in thickness of the guide member 14 in FIGS. 3 and 4. The upper surface 19 of the guide member 14 therefore is tapered or sloped with respect to the support surface 12. A cone section 16 rests on the tapered surface of the guide member 14 and a guide slot 17 (FIG. 5) is formed between the cone section 16 and the guide member 14. As shown in FIGS. 5 and 1, a step 18 is formed at the end of the guide slot 17. The step 18 can be formed by milling a step in the tapered surface 19 of the guide member 14, in the bottom surface of the cone section 16, or in both the tapered surface 19 and the cone section 16. The cone section 16 therefore is held above the tapered surface 19 of the guide member 14 by a preselected distance which is determined by the height of the step 18. The width of the guide slot 17 is therefore determined by the height of the step 18. Preferably the preselected distance between the tapered surface 19 and the cone section 16 is substantially equal to the thickness of the material to be formed in the device so that the material readily penetrates the guide slot 17 but is snugly held within the slot.

A bending means, which preferably is a roller 21, is rotatably supported in the actuating means 13 at a preselected distance from the cone section 16. The preselected distance preferably is substantially equal to the thickness of the material to be formed. If desired the mounting of the roller 21 and the actuating means 13 can be adjustable to allow for different thicknesses of material to be bent. The width of the guide slot 17 between the tapered surface 19 and the cone section 16 can also be made adjustable. The degree of taper of the cone section 16 is selected to form a very sharp bend at one end of the piece of material being bent and a much wider bend at the other end of the material. When the device is used to test the adherence of the oxide coating to the steel used for forming shadow masks for cathode ray tubes the degree of taper preferably is two degrees, as measured from the longitudinal axis of the cone section. The degree of taper on the tapered surface 19 of the guide member 14 is the same as that of the cone section 16. Additionally, the roller 21 is angularly mounted in the actuating means 13 so that the roller 21 is substantially parallel to the surface 22 of the cone section 16. Accordingly, the angular disposition of the roller 21 is determined by the degree of taper of the cone section.

Figure 2:
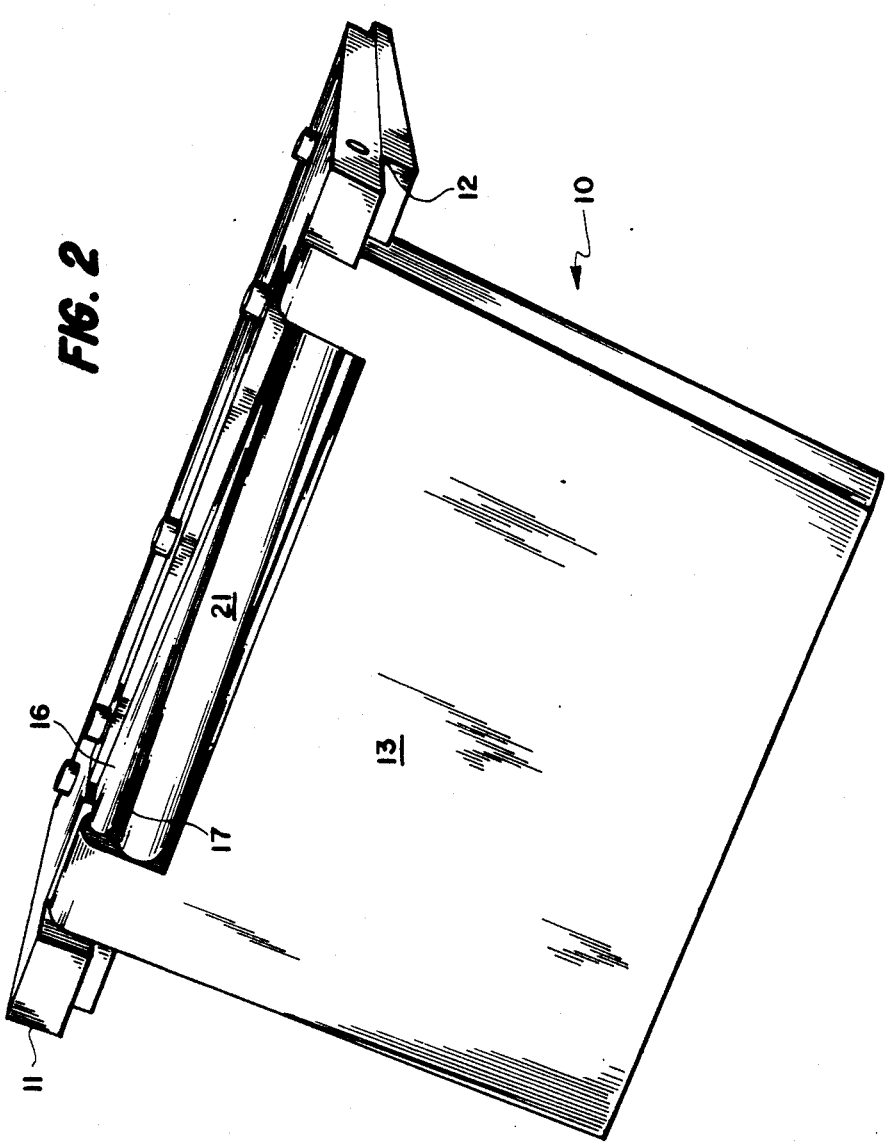
FIG. 2 is an isometric view showing the preferred embodiment in a position to receive an article to be tested for adherence.

As shown in FIG. 2, the roller 21 is rotatably mounted in the actuating means 13. The cone section 16 is a wedge shaped member and the surface 22 therefore is a rounded edge, which as shown in FIGS. 3 and 4, faces the roller 21.

In FIG. 1, the step 18 between the tapered surface 19 and cone section 16 is shown in phantom. The step 18 is angularly disposed with respect to the rounded edge 22 of the cone section 16. The angular disposition is determined by the change in the radius of the rounded edge 22 which is necessitated by the taper of the cone section 16.

Figure 6:
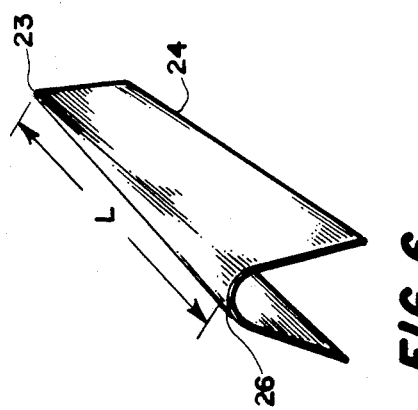
FIG. 6 shows a substrate after bending with the preferred embodiment.

In FIG. 2, the actuating means 13 is rotated with respect to the base member 11, the direction of rotation from the position shown in FIGS. 3 and 4 is downwardly, or counterclockwise. The guide slot 17 is fully exposed and is ready to receive a material to be formed by the device 10. The material to be formed is inserted into the guide slot 17 until contact is made with the full length of the step 18. The actuating means 13 is then rotated clockwise 180° to be approximately at right angles with respect to the base member 11. During the motion of the actuating means 13 the roller 21 presses the material being formed against the rounded edge 22 of the wedge shaped member 16 and rolls the material around the cone section 16. After the material is completely bent the actuating means 13 is returned to the position shown in FIG. 2 and the bent material is removed from the guide slot 17. In this manner a piece of formed material, such as the piece 24 shown in FIG. 6, is formed. One end 23 of the piece 24 has a very sharp bend while the other end 26 has a much more gradual and rounded bend. The bending occurs in a direction such that the coating lies on the outside of the bent piece 24. The ductility of the coating usually is different from that of the substrate and typically is more brittle than a metal substrate. Accordingly, when the metal is bent the coating has a tendency to break due to the bending. The radius of curvature increases in accordance with the angle of the cone section 16. Accordingly, flaking of the coating from the substrate is much more likely to occur in the proximity of the narrow end 23 than in the proximity of the wider end 26. This phenomena can be used as a quantitative test for measuring the adherence of the coating to the substrate. Thus, for a given length L of substrate, the adherence can be expressed as the point where flaking ceases to occur along the bend formed by the cone section 16. The adherence can thus be measured in the manner shown in Table I.

TABLE I

| SAMPLE | ADHERENCE NUMBER |
| --- | --- |
| A | 0 |
| B | 0.1 |
| C | 0.2 |
| D | 0.3 |
| E | 0.4 |
| F | 0.5 |
| G | 0.6 |
| H | 0.7 |
| I | 0.8 |
| J | 0.9 |

In Table I sample A has an adherence number of 0, this indicates that no flaking occurred anywhere along the length of the piece member 24 of FIG. 6, this is the ideal adherence condition. Sample B has an adherence number of 0.1 indicating that flaking stopped at a point which is 1/10th of the total length of the piece 24, beginning the measurement at the narrow end 23. Sample J has an adherence number of 0.9, indicating that 90% of the length of the bent piece 24 flaked and that this sample is the worse sample. Accordingly, with the invention, a table similar to Table I can be statistically established for a given coating on a given substrate. After the table is statistically established, samples of product which are being manufactured by the process in question can be periodically tested to verify the adherence of the coating to the substrate and to assure that the processing has not deviated and begun to produce poor product. In many instances it may be necessary to investigate the flaking using magnifying lenses or microscopes.

What is claimed is:

1. A device for testing the adherence of a coating layer to a material comprising:
    a base member having a support surface;
    a guide member supported by said support surface, said guide member having a tapered thickness to form a tapered surface;
    a cone section, having a preselected angle, supported on said tapered surface at a preselected distance from said tapered surface for forming a guide slot for guiding said material between said cone section and said tapered surface;
    actuation means pivotally attached to said base member in the proximity of said cone section;
    bending means actuated by said actuation means for bending said material around said cone section and for forming a tapered bend in said material.

2. The device of claim 1 wherein said bending means includes a roller rotatably supported by said bending means and arranged substantially parallel to said cone section.

3. The device of claim 2 further including a step formed in at least one of said cone section or said tapered surface for controlling the penetration of said material into said guide slot.

4. The device of claim 3 wherein said preselected distance is substantially equal to the thickness of said material.

5. The device of claim 4 wherein said cone section is spaced from said roller by a distance substantially equal to the thickness of said material.

6. The device of claim 3 wherein said step is angularly disposed with respect to the surface of said cone section.

7. The device of claim 6 wherein said angular disposition of said step with respect to said cone section varies proportionally to the angle of said cone section.

8. The device of claim 2 wherein said cone section is a wedge shaped member having a rounded edge facing said roller.

9. The device of claim 8 wherein said cone section is spaced from said roller by a distance substantially equal to the thickness of said material.

10. The device of claim 9 further including a step formed in at least one of said cone section or said tapered surface for controlling the penetration of said material into said guide slot.

11. The device of claim 10 wherein said preselected distance is substantially equal to the thickness of said material.

* * * * *